United States Patent
Beier et al.

(10) Patent No.: US 9,439,442 B2
(45) Date of Patent: *Sep. 13, 2016

(54) METHOD OF PREPARING A DOUGH-BASED PRODUCT

(71) Applicant: Novozymes A/S, Bagsvaerd (DK)

(72) Inventors: Lars Beier, Bagsvaerd (DK); Esben Peter Friis, Bagsvaerd (DK); Henrik Lundquist, Malmo (SE)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/955,490

(22) Filed: Dec. 1, 2015

(65) Prior Publication Data

US 2016/0081357 A1  Mar. 24, 2016

Related U.S. Application Data

(60) Continuation of application No. 13/742,998, filed on Jan. 16, 2013, now Pat. No. 9,226,510, which is a continuation of application No. 12/964,189, filed on Dec. 9, 2010, now abandoned, which is a division of application No. 11/575,644, filed as application No. PCT/DK2005/000602 on Sep. 23, 2005, now abandoned.

(60) Provisional application No. 60/614,826, filed on Sep. 30, 2004.

(30) Foreign Application Priority Data

Sep. 24, 2004 (DK) ................................ 2004 01458

(51) Int. Cl.
| | |
|---|---|
| *C12N 9/28* | (2006.01) |
| *C12N 15/00* | (2006.01) |
| *A23L 1/10* | (2006.01) |
| *A21D 8/04* | (2006.01) |
| *A21D 13/00* | (2006.01) |
| *C12N 9/26* | (2006.01) |

(52) U.S. Cl.
CPC ........... *A21D 8/042* (2013.01); *A21D 13/0096* (2013.01); *C12N 9/2411* (2013.01); *C12N 9/2417* (2013.01); *C07K 2299/00* (2013.01); *C12Y 302/01133* (2013.01)

(58) Field of Classification Search
CPC ........................... C12N 9/2411; C12N 9/2417
See application file for complete search history.

(56) References Cited

U.S. PATENT DOCUMENTS

| | | |
|---|---|---|
| 3,026,205 A | 3/1962 | Stone |
| 4,500,548 A | 2/1985 | Silva |
| 5,409,717 A | 4/1995 | Apicella |
| 6,162,628 A | 12/2000 | Cherry |
| 6,482,622 B1 | 11/2002 | Cherry |
| 7,892,806 B2 | 2/2011 | Svendsen et al. |
| 8,361,526 B2 | 1/2013 | Beier et al. |

FOREIGN PATENT DOCUMENTS

| | | |
|---|---|---|
| WO | 91/04669 A1 | 4/1991 |
| WO | 99/43794 A1 | 9/1994 |
| WO | 00/29591 A1 | 5/2000 |
| WO | 2006/012899 A1 | 2/2006 |

OTHER PUBLICATIONS

Branden et al, 1991, Intro Protein Structure, 247.
Conforti et al, 1998, J Food Qual 21(2), 85-94.
Dauter et al, 1999, Protein Data Bank—3d struc-Novamyl identifiers 1QHO and 1QHP.
Hyun-Ju et al, 1998, Eur J Biochem 253, 251-262.
Rosell et al, 2001, J Agric Food Chem 49(6), 2973-2977.
Sternhagen et al, 1994, Cereal Chem 71(6), 560-563.
Takase et al, 1992, Biochim Biophys Acta 1120, 281-288.
Telloke, 1985, Starch 37(1), 17-22.

*Primary Examiner* — Yong Pak
(74) *Attorney, Agent, or Firm* — Kristin McNamara

(57) ABSTRACT

Dough with a high sucrose content (such as cake dough) tends to inhibit the activity of an anti-staling amylase such as Novamyl, making it less effective to prevent the staling of dough-based products with high sucrose content such as cakes. A good anti-staling effect in cakes can be achieved by using a carefully selected anti-staling amylase with certain properties.

Analysis of a 3D structure of Novamyl shows that sucrose may inhibit by binding in the active site. Sucrose docks into the active site of Novamyl differently from the substrate or inhibitor in published models 1QHO and 1QHP. This finding is used to design sucrose-tolerant variants.

10 Claims, 1 Drawing Sheet

```
ATOM      1  C1  GLC A   1      39.217  71.096  23.310  1.00 53.03           C
ATOM      2  C2  GLC A   1      38.281  69.893  23.579  1.00 55.06           C
ATOM      3  O2  GLC A   1      37.370  70.251  24.614  1.00 58.15           O
ATOM      4  C3  GLC A   1      39.115  68.665  24.014  1.00 52.01           C
ATOM      5  O3  GLC A   1      38.239  67.559  24.250  1.00 51.59           O
ATOM      6  C4  GLC A   1      40.134  68.335  22.918  1.00 53.38           C
ATOM      7  O4  GLC A   1      41.075  67.354  23.379  1.00 56.10           O
ATOM      8  C5  GLC A   1      40.910  69.552  22.419  1.00 55.06           C
ATOM      9  O5  GLC A   1      40.130  70.771  22.258  1.00 55.28           O
ATOM     10  C6  GLC A   1      41.528  69.246  21.045  1.00 52.65           C
ATOM     11  O6  GLC A   1      42.190  70.422  20.599  1.00 38.28           O
ATOM     12  H01 GLC A   1      41.470  68.299  20.510  1.00 52.65           H
ATOM     13  H02 GLC A   1      38.649  71.976  23.008  1.00 53.03           H
ATOM     14  H03 GLC A   1      37.734  69.638  22.672  1.00 55.06           H
ATOM     15  H04 GLC A   1      37.860  70.513  25.396  1.00 58.15           H
ATOM     16  H05 GLC A   1      39.655  68.880  24.937  1.00 52.01           H
ATOM     17  H06 GLC A   1      37.543  67.825  24.856  1.00 51.59           H
ATOM     18  H07 GLC A   1      41.666  67.115  22.661  1.00 56.10           H
ATOM     19  C1  FRU A   2      39.472  73.740  24.328  1.00 56.70           C
ATOM     20  O1  FRU A   2      39.013  73.640  22.974  1.00 60.98           O
ATOM     21  C2  FRU A   2      40.511  72.650  24.697  1.00 60.03           C
ATOM     22  O2  FRU A   2      39.917  71.335  24.487  1.00 54.05           O
ATOM     23  C3  FRU A   2      41.038  72.717  26.169  1.00 56.66           C
ATOM     24  O3  FRU A   2      40.143  72.012  27.049  1.00 57.01           O
ATOM     25  C4  FRU A   2      42.371  71.945  26.006  1.00 56.00           C
ATOM     26  O4  FRU A   2      43.252  72.139  27.103  1.00 53.30           O
ATOM     27  C5  FRU A   2      42.866  72.599  24.701  1.00 54.87           C
ATOM     28  O5  FRU A   2      41.705  72.741  23.843  1.00 54.62           O
ATOM     29  C6  FRU A   2      43.903  71.816  23.946  1.00 55.79           C
ATOM     30  O6  FRU A   2      44.464  72.647  22.938  1.00 54.56           O
ATOM     31  H01 FRU A   2      43.759  73.046  22.423  1.00 54.56           H
ATOM     32  H02 FRU A   2      38.615  73.643  24.994  1.00 56.70           H
ATOM     33  H03 FRU A   2      38.363  74.325  22.804  1.00 60.98           H
ATOM     34  H04 FRU A   2      41.133  73.718  26.592  1.00 56.66           H
ATOM     35  H05 FRU A   2      40.267  71.066  26.941  1.00 57.01           H
ATOM     36  H06 FRU A   2      42.287  70.859  25.973  1.00 56.00           H
ATOM     37  H07 FRU A   2      42.807  71.896  27.918  1.00 53.30           H
ATOM     38  H08 FRU A   2      43.345  73.538  24.976  1.00 54.87           H
ATOM     39  H09 FRU A   2      43.440  70.944  23.487  1.00 55.79           H
ATOM     40  H10 FRU A   2      44.686  71.486  24.630  1.00 55.79           H
ATOM     41  H11 FRU A   2      39.962  74.708  24.436  1.00 56.70           H
```

METHOD OF PREPARING A DOUGH-BASED PRODUCT

CROSS-REFERENCE TO RELATED APPLICATIONS

This application is a continuation of U.S. application Ser. No. 13/742,998 filed on Jan. 16, 2013 (now allowed), which is a continuation of U.S. application Ser. No. 12/964,189 filed Dec. 9, 2010 (abandoned), which is a divisional of U.S. application Ser. No. 11/575,644 filed on Mar. 20, 2007 (abandoned), which is a 35 U.S.C. 371 national application of PCT/DK2005/000602 filed Sep. 23, 2005, which claims priority or the benefit under 35 U.S.C. 119 of Danish application no. PA 2004 01458 filed Sep. 24, 2004 and U.S. provisional application No. 60/614,826 filed Sep. 30, 2004, the contents of which are fully incorporated herein by reference.

SEQUENCE LISTING AND DEPOSITED MICROORGANISMS

Sequence Listing

The present invention comprises a sequence listing.

Deposit of Biological Material

None.

FIELD OF THE INVENTION

The present invention relates to the use of anti-staling amylases in the preparation of dough or dough-based edible products with a high sucrose content.

BACKGROUND OF THE INVENTION

U.S. Pat. No. 3,026,205 describes a process of producing baked confections and the products resulting therefrom by alpha-amylase.

WO 9104669 describes the use of a maltogenic alpha-amylase to retard the staling of baked products such as bread; the maltogenic alpha-amylase described therein is commercially available under the tradename Novamyl® (product of Novozymes A/S). U.S. Pat. No. 6,162,628 describes Novamyl variants and their use for the same purpose. Three-dimensional structures of Novamyl are published in U.S. Pat. No. 6,162,628 and in the Protein Data Bank (available at http://www.rcsb.org/pdb/) with identifiers 1QHO and 1QHP.

SUMMARY OF THE INVENTION

The inventors have found that a high sucrose content dough (such as cake dough) tends to inhibit the activity of an anti-staling amylases such as Novamyl, making it less effective to prevent the staling of dough-based products with high sucrose content such as cakes. They have found that a good anti-staling effect in cakes can be achieved by using a carefully selected anti-staling amylase with certain properties, and they have identified such amylases.

By analyzing a 3D structure of Novamyl, the inventors further found that sucrose may inhibit by binding in the active site. They have found that sucrose docks into the active site of Novamyl differently from the substrate or inhibitor in published models 1QHO and 1QHP, and they have used this finding to design sucrose-tolerant variants.

Accordingly, the invention provides a method of preparing dough or a dough-based edible product (e.g. a baked product) by adding a sucrose-tolerant anti-staling amylase. It also provides novel sucrose tolerant variants of a maltogenic alpha-amylase.

BRIEF DESCRIPTION OF THE DRAWINGS

FIG. 1 shows the cartesian coordinates for the sucrose atoms in this binding configuration, using the coordinate system of the x-ray structure 1QHO.pdb.

DETAILED DESCRIPTION OF THE INVENTION

Maltogenic Alpha-Amylase and Sucrose Docking

A maltogenic alpha-amylase (EC 3.2.1.133) having more than 70% identity (particularly more than 80% or 90%, such as at least 95% or 96% or 97% or 98% or 99%) with the Novamyl sequence shown as SEQ ID NO: 1 may be used as the parent enzyme for designing sucrose tolerant variants. Amino acid identity may be calculated as described in U.S. Pat. No. 6,162,628.

For Novamyl (SEQ ID NO: 1), a 3D structure including a substrate or inhibitor as described in U.S. Pat. No. 6,162,628 or in the Protein Data Bank with the identifier 1QHO or 1QHP may be used. Alternatively, a Novamyl variant may be used, such as a variant described in U.S. Pat. No. 6,162,628 or in this specification, e.g. the variant F188L+D261G+T288P. A 3D structure of a variant may be developed from the Novamyl structure by known methods, e.g. as described in T. L. Blundell et al., Nature, vol. 326, p. 347 ff (26 Mar. 1987); J. Greer, Proteins: Structure, Function and Genetics, 7:317-334 (1990); or Example 1 of WO 9623874.

The inventors found that sucrose may inhibit Novamyl by binding in the active site. Docking of sucrose into the active site of Novamyl (using the software GOLD version 2.1.2, Cambridge Crystallographic Data Centre, 12 Union Road, Cambridge, CB2 1EZ, UK and the protein part of the x-ray structure 1QHO.pdb) reveals a specific binding configuration as unique to sucrose. The cartesian coordinates for the sucrose atoms in this binding configuration, using the coordinate system of the x-ray structure 1QHO.pdb are given in FIG. 1.

Maltogenic Alpha-Amylase Assay

The activity of a maltogenic alpha-amylase may be determined using an activity assay such as the MANU method. One MANU (Maltogenic Amylase Novo Unit) is defined as the amount of enzyme required to release one micro-mole of maltose per minute at a concentration of 10 mg of maltotriose substrate per ml in 0.1 M citrate buffer at pH 5.0, 37° C. for 30 minutes.

Amino Acid Alterations

The amino acid sequence of a maltogenic alpha-amylase may be altered to decrease the sucrose inhibition. The inventors found that the alteration may be made at an amino acid residue having at least one atom within 4 Angstroms from any of the sucrose atoms when the sucrose molecule is docked in the 3D structure of the maltogenic alpha-amylase. Using the Novamyl structure 1QHO and the sucrose docking in FIG. 1, the following Novamyl residues are within 4 Å: K44, N86, Y89, H90, Y92, W93, F188, T189, D190, P191, A192, F194, D372, P373, R376.

Further the following positions have been identified as relevant: I15, R81, T87, G88, L196, N371 or N375 of SEQ ID NO: 1.

The alteration may be a substitution or deletion of one or more of the selected residues, or one or more residues (particularly 1-4 residues or 5-6 residues) can be inserted adjacent to a selected residue.

The substitution may be with a smaller or larger residue. A substitution to increase the size of the residue may diminish the space obtained by the docked sucrose molecule thereby preventing the binding of sucrose. Amino acid residues are ranked as follows from smallest to largest: (an equal sign indicates residues with sizes that are practically indistinguishable):

G<A=S=C<V=T<P<L=I=N=D=M<E=Q<K<H<R<F<Y<W

The substitution may also be such as to eliminate contacts with the sucrose molecule, in particular by moving or removing potential sites of hydrogen bonding or Van der Waals interactions.

The substitution may particularly be with another residue of the same type where the type is negative, positive, hydrophobic or hydrophilic. The negative residues are D,E, the positive residues are K/R, the hydrophobic residues are A,C,F,G,I,L,M,P,V,W,Y, and the hydrophilic residues are H,N,Q,S,T.

Some particular examples of substitutions are I15T/S/V/L, R18K, K44R/S/T/Q/N, N86Q/S/T, T87N/Q/S, G88A/S/T, Y89W/F/H, H90W/F/Y/R/K/N/Q/M, W93Y/F/M/E/G/V/T/S, F188H/L/I/T/G/V, D190E/Q/G, A192S/T, F194S/L/Y, L196F, N371K/R/F/Y/Q, D372E/Q/S/T/A and N375S/T/D/E/Q.

Examples of deletions are deletion of residue 191 or 192. An example of an insertion is Ala inserted between 192 and 193.

The polypeptide may include other alterations compared to Novamyl (SEQ ID NO: 1), e.g. alterations to increase the thermostability as described in U.S. Pat. No. 6,162,628.

Nomenclature for Amino Acid Alterations

In this specification, an amino acid substitution is described by use of one-letter codes, e.g. K44R. Slashes are used to indicate alternatives, e.g. K44R/S/T/Q/N to indicate substitution of K44 with R or S etc. P191* indicates a deletion of P191. *192aA indicates insertion of one Ala after A192. Commas are used to indicate multiple alterations in the sequence, e.g. F188L,D261G,T288P to indicate a variant with three substitutions.

Properties of Anti-Staling Amylase for Use with Sucrose

The amylase for use in high-sucrose dough may be selected so as to have mainly exo-amylase activity. More specifically, the amylase hydrolyzes amylose so that the average molecular weight of the amylose after 0.4-4% hydrolysis is more than 50% (particularly more than 75%) of the molecular weight before the hydrolysis.

Thus, the amylase may hydrolyze amylose (e.g. wheat amylose or synthetic amylose) so that the average molecular weight of the amylose after 0.4-4% hydrolysis (i.e. between 0.4-4% hydrolysis of the total number of bonds) is more than 50% (particularly more than 75%) of the value before the hydrolysis. The hydrolysis can be conducted in a 1.7% amylose solution by weight at suitable conditions (e.g. 10 minutes at 60° C., pH 5.5), and the molecular weight distribution before and after the hydrolysis can be determined by HPLC. The test may be carried out as described in C. Christophersen et al., Starch 50 (1), 39-45 (1998).

An exo-amylase for use in high-sucrose dough may have a specified sugar tolerance. Compared to its activity in the absence of sucrose, the amylase may have more than 20% activity at 10% sugar, more than 10% activity at 20% sucrose, or more than 4% activity at 40% sucrose. The sugar tolerance may be determined as described in the examples.

The exo-amylase may have optimum activity in the pH range 4.5-8.5. It may have sufficient thermostability to retain at least 20% (particularly at least 40%) activity after 30 minutes incubation at 85° C. at pH 5.7 (50 mM Na-acetate, 1 mM $CaCl_2$) without substrate.

The exo-amylase may be added to the dough in an amount corresponding to 1-100 mg enzyme protein per kg of flour, particularly 5-50 mg per kg.

The exo-amylase may be non-liquefying. This can be determined by letting the exo-amylase act on a 1% wheat starch solution until the reaction is complete, i.e. addition of fresh enzyme causes no further degradation, and analyzing the reaction products, e.g. by HPLC. Typical reaction conditions are e.g. 0.01 mg enzyme per ml starch solution for 48 hours. The exo-amylase is considered non-liquefying if the amount of residual starch after the reaction is at least 20% of the initial amount of starch.

The exo-amylase may have maltogenic alpha-amylase activity (EC 3.2.1.133). The exo-amylase may be the amylase described in DK PA 2004 00021, or it may be a Novamyl variant described in this specification.

Dough and Dough-Based Edible Product

The dough may have a sucrose content above 10% by weight, particularly above 20% or 30%, e.g. 30-40%. The flour content is typically 25-35% by weight of total ingredients. The dough may be made by a conventional cake recipe, typically with cake flour, sugar, fat/oil and eggs as the major ingredients. It may include other conventional ingredients such as emulsifiers, humectants, gums, starch and baking powder. It generally contains such ingredients as soft wheat flour, milk or other liquids, sugar, eggs, chemical leaveners, flavor extracts and spices, as well as others that may or may not include shortening.

The dough is generally heat treated, e.g. by baking or deep frying to prepare an edible product such as cakes including pound cake, yellow and white layer cakes, cakes containing chocolate and cocoa products, sponge cakes, angel food cake, fruit cakes and foam-type cakes and doughnuts.

EXAMPLES

Example 1

Sucrose Tolerance of Novamyl Variants

The amylase activity of a number of polypeptides were tested by incubation with Phadebas tablets (product of Pharmacia®) for 15 minutes at 60° C. in the presence of sucrose at various concentrations (in % by weight). The results are expressed in % of the result without sugar:

| Alterations compared to SEQ ID NO: 1 | 0% sucrose | 10% sucrose | 20% sucrose | 40% sucrose |
|---|---|---|---|---|
| None | 100 | 13 | 6 | 1.5 |
| F188L, D261G, T288P | 100 | 27.5 | 14.5 | 6 |
| F194S | 100 | 31.5 | 18.5 | 7.5 |
| L196F | 100 | 69 | 42 | 23 |
| D190G | 100 | 65 | 43 | 21 |

Example 2

Sucrose Tolerance of Novamyl Variants

A number of polypeptides were tested as in Example 1. The results are expressed as activity with 10% sucrose in % of the activity without sucrose:

| Alterations compared to SEQ ID NO: 1 | Sugar tolerance |
| --- | --- |
| None | 15 |
| D261G, T288P | 24 |
| F188L, D261G, T288P | 35 |
| T288P | 56 |
| Y89F, D261G, T288P | 42 |
| N86V, F188L, D261G, T288P | 37 |
| Y89F, F188L, D261G, T288P | 38 |
| Y89H, F188L, D261G, T288P | 50 |
| N86T, F188L, D261G, T288P | 49 |
| F194S, D261G, T288P | 47 |
| L196F | 65 |
| D261G, T288P, D372V | 62 |
| Q184H, N187D, F194Y | 47 |
| D190G | 66 |
| N86G, Y89M, F188L, D261G, T288P | 47 |
| F188L, D190G, D261G, T288P | 68 |
| A192Q, D261G, T288P, S446A | 46 |
| F188H | 49 |
| P191* | 42 |
| A192* | 51 |
| A192*, G193* | 67 |
| *192aA | 44 |
| N86K, F252L, D261G, T288P | 49 |
| F194Y, L225S, D261G, T288P | 49 |
| F194L, D261G, T288P | 54 |
| F194S, D261G, T288P, P642Q | 60 |
| D261G, T288P, N375S | 58 |
| F188T | 37 |
| F188G | 36 |
| F188V | 41 |
| A192R, F194L, D261G, T288P, G469R | 60 |
| A192G, D261G, T288P | 41 |
| Y89F, D261G, T288P, I290V, N375S | 60 |

The following variants are also considered of interest in the context of the present invention:

| Alterations compared to SEQ ID NO: 1 |
| --- |
| I15T, N86K, P191S, D261G, T288P |
| I15T, P191S, D261G, T288P |
| I15T, P191S, Y258F, D261G, T288P, N375S, Y549C, Q648H |
| I15T, G153R, P191S, D261G, T288P, N371K, K645R |

Example 3

Sucrose Tolerance and Thermostability of Amylases

The following amylases were tested for thermostability and sugar tolerance: bacterial alpha-amylase from *B. amyloliquefaciens* (BAN™, product of Novozymes NS), fungal alpha-amylase from *A. oryzae* (Fungamyl®, product of Novozymes A/S), maltogenic alpha-amylase having the sequence of SEQ ID NO: 1 (Novamyl®, product of Novozymes A/S), a Novamyl variant having SEQ ID NO: 1 with the substitutions F188L+D261G+T288P, and bacterial alpha-amylase from *B. licheniformis* (Termamyl®, product of Novozymes A/S).

Exo-Amylase Activity

The five amylases were tested for exo-amylase activity as described above. The results show that Novamyl and the Novamyl variant had exo-amylase activity by this test, and the other three did not.

Thermostability

Each amylase was incubated at 85° C. at pH 5.7 (50 mM Na-acetate, 1 mM $CaCl_2$) without substrate, and the amylase activity was measured after 0, 15, 30 and 60 minutes heat treatment. The results are expressed as residual activity in % of the initial activity:

|  | 0 | 15 | 30 | 60 |
| --- | --- | --- | --- | --- |
| BAN | 100 | 3 | 1 | 0 |
| Fungamyl | 100 | 0 | 0 | 0 |
| Novamyl | 100 | 51 | 29 | 13 |
| Novamyl variant | 100 | 64 | 48 | 54 |
| Termamyl | 100 | 100 | 71 | 85 |

The results show that the Novamyl variant and Termamyl were not deactivated by the heat-treatment. BAN and Fungamyl lose all their activity after 15 min while Novamyl loses it gradually with heat-treatment time.

Sucrose Tolerance

The experiment was repeated in 10% sucrose solution. The results are expressed as residual activity in % of the initial activity without sucrose:

|  | 0 | 15 | 30 | 60 |
| --- | --- | --- | --- | --- |
| BAN | 93 | 2 | 1 | 0 |
| Fungamyl | 31 | 0 | 0 | 0 |
| Novamyl | 7 | 6 | 1 | 3 |
| Novamyl variant | 21 | 19 | 14 | 16 |
| Termamyl | 116 | 112 | 97 | 82 |

The results show that BAN and Termamyl were not inhibited by sugar while Fungamyl and the Novamyl variant were somewhat inhibited, and Novamyl was heavily inhibited by sugar. The combination of sugar and heat-treatment shows that the Novamyl variant and Termamyl could be active during baking of cakes. Termamyl and the Novamyl variant fulfill the criterion for thermostability and sugar tolerance used in this invention.

Example 4

Preparation of Sponge Cake with Amylase

Sponge cakes were made with addition of amylase as follows: BAN (0.83. 8.3 or 83 mg/kg flour), Novamyl (1.3 or 13 mg/kg flour) or the Novamyl variant used in Example 1 (1, 10 or 100 mg/kg flour). A control cake was made without amylase.

The cakes were baked according to the High Ratio Sponge Sandwich Cake (HRSSC) method. After baking, cakes were cooled down for 60-120 minutes, and the cakes were stored at room temperature in sealed plastic bags filled with nitrogen until analysis. The cakes were evaluated on day 1, 3, 7 or 23.

Texture profile analysis (TPA) was performed as described in Bourne M. C. (2002) 2. ed., Food Texture and Viscosity: Concept and Measurement. Academic Press. The results showed that the increase in hardness was slower with increasing dosage of the Novamyl variant. The addition of BAN or Novamyl had only a slight effect, and only at the highest dosage.

The cohesiveness of the cakes decreased with storage time. The addition of the Novamyl variant delayed this decrease. The addition of BAN or Novamyl had a slight effect, and only at the highest dosage.

Water mobility was characterized by low field NMR. The addition of the Novamyl variant and BAN increased the mobility, indicating that the two amylases were able to keep the cakes more moist. Novamyl had virtually no effect.

A small sensory evaluation of softness and moistness was performed on day 13 for the 3 cakes with the Novamyl variant and the control cake. The cakes were evaluated regarding three parameters; Firmness, Moistness and preferability. The control was the firmest, driest and least preferred. The higher dosage of the Novamyl variant, the less firm (softer), moister and better liked.

A large panel sensory evaluation was performed on day 13. It was a paired comparison test where a control cake was compare to the cake with the Novamyl variant at the highest dosage. A 30-member panel was asked two questions (1) Which cake is moister and (2) which cake is fresher. All panel members agreed on that the cake with the Novamyl variant was moister and fresher. The preference was significant at a significance level above 99.999%.

To summarize, the data show that the Novamyl variant had anti-staling properties and was able to improve moistness perception and moistness measured by NMR. The two other amylases had only a slight effect.

Example 5

High-Ratio Unit Cakes

Cakes were made with addition of amylase as follows: BAN (0.83. 8.3 or 83 mg/kg flour) or the Novamyl variant used in Example 1 (1, 10 or 100 mg/kg flour). A control cake was made without amylase.

Cakes were baked according to the High ratio unit cake (HRUC) method. After baking, the cakes were cooled down for 60-120 minutes, and the cakes were stored at room temperature in sealed plastic bags filled with Nitrogen until analysis. The cakes were evaluated on day 7, 20 and 34 by the same methods as in the previous example.

The increase in hardness was slower with the Novamyl variant at the highest dosage. The addition of BAN to the cake resulted in a low volume and a doughy cake which gave poor results in hardness measurements.

The addition of the Novamyl variant delayed the decrease in cohesiveness while BAN did not influence it at all.

The Novamyl variant and BAN were able to keep the cake more moist than the control. This increase in mobility of the free water could partly be explained by the cakes with BAN and the Novamyl variant being able to retain the moisture content.

A small sensory evaluation on day 34 showed that the cake with the Novamyl variant at the highest dosage was clearly better than the control cake; it was more moist and it was less crumbly.

Over-all, there was an anti-staling effect of the Novamyl variant at the high dosage, similar to the effect on sponge cakes in the previous example. The staling of HRUC cakes was slower than Sponge cakes but it was still evident that the Novamyl variant had an anti-staling effect. The anti-staling effect was seen with texture analysis, NMR and sensory evaluation. BAN showed anti-staling effects in HRUC but it was sensitive to over-dosage which resulted in cake collapse and a doughy cake.

Example 6

Sponge Cake

Sponge cakes were made with addition of the amylase of DK PA 2004 00021 at dosages 0.5, 1, 2, 5 and 20 mg/kg flour and a control cake without amylase.

Texture and NMR was measured on day 1, 7 and 13. The addition of the amylase reduced the increase in firmness, especially at the highest dosage. The amylase also had a beneficial effect on the mobility of water which was correlated with the moistness of the cake.

A blind sensory ranking evaluation performed on day 14 showed a ranking according to the dosage, the higher dosage the more soft and moist cake. The most preferred cake was the one with the highest dosage.

Example 7

Baking Procedure Tegral Allegro Cake

Recipe

The following recipe was used:

|   | % |
|---|---|
| Tegral Allegro mix* | 100 |
| Pasteurized whole egg | 50 |
| Butter | 50 |
| Enzymes | According to trial. 0 or 25 mg/kg flour. |

*commercially available from Puratos NV/SA, Groot-Bijgaarden, Belgium

Procedure

The ingredients were scaled into a mixing bowl and mixed using an industrial mixer (e.g. Bjørn AR 5 A Varimixer) with a suitable paddle speed. 300 g of the dough was poured into forms. The cakes are baked in a suitable oven (e.g. Sveba Dahlin deck oven) for 45 min. at 180° C. The cakes were allowed to cool down at room temperature for 1 hour.

The volume of the cakes was determined when the cakes had cooled down using the rape seed displacement method. The cakes were packed under nitrogen in sealed plastic bags and stored at room temperature until analysis.

The cakes were evaluated on day 1, 7 and 14, two cakes were used at each occasions.

The cohesiveness and hardness of the cakes was evaluated with Texture analyser and the water mobility was characterized by low field NMR.

The Texture profile analysis (TPA) was performed as described in Bourne M. C. (2002) 2. ed., Food Texture and Viscosity: Concept and Measurement. Academic Press.

The mobility of free water was determined as described by P. L. Chen, Z. Long, R. Ruan and T. P. Labuza, Nuclear Magnetic Resonance Studies of water Mobility in Bread during Storage. Lebensmittel Wissenschaft and Technologie 30, 178-183 (1997). The mobility of free water has been described in literature to correlate to moistness of bread crumb.

Result

Compared to cakes with no addition of enzymes the volume of the cakes is not affected by the addition of the reference enzyme (SEQ ID NO.: 1) nor by the addition of variants hereof, i.e. the cakes did not collapse upon addition of enzyme.

The cohesiveness of the cakes decreased with storage time. The addition of variants of SEQ ID NO: 1 delayed this decrease as can be seen in Table 1.

TABLE 1

Change in Cohesiveness [gs/gs] with storage time of cakes with 25 mg protein enzyme per kg flour

| Enzyme | Day 1 | Day 7 | Day 14 |
| --- | --- | --- | --- |
| No enzyme | 0.44 | 0.35 | 0.32 |
| Seq ID No: 1 | 0.43 | 0.38 | 0.36 |
| F188L, D261G, T288P | 0.46 | 0.42 | 0.41 |
| Y89F, D261G, T288P | 0.45 | 0.43 | 0.39 |
| N86G, Y89M, F188L, D261G, T288P | 0.44 | 0.42 | 0.38 |
| T288P | 0.44 | 0.40 | 0.41 |
| F194S, D261G, T288P | 0.47 | 0.43 | 0.42 |
| D261G, T288P, D372V | 0.46 | 0.43 | 0.37 |
| A192Q, D261G, T288P, S446A | 0.44 | 0.42 | 0.39 |
| A192R, F194L, D261G, T288P, G469R | 0.47 | 0.44 | 0.42 |
| A192G, D261G, T288P | 0.46 | 0.42 | 0.39 |
| N86K, F252L, D261G, T288P | 0.45 | 0.41 | 0.39 |
| F194L, D261G, T288P | 0.45 | 0.42 | 0.42 |
| F194S, D261G, T288P, P642Q | 0.44 | 0.40 | 0.39 |
| Y89F, D261G, T288P, I290V, N375S | 0.43 | 0.42 | 0.40 |

The free water mobility is correlated with the moist perception of the cake crumb, it decreases with time. The addition of the Novamyl variants increased the mobility compared to the control, indicating that the amylases were able to keep the cakes more moist. Results are listed in Table 2.

TABLE 2

Change in free water mobility [micros] with storage time of cakes with 25 mg protein enzyme per kg flour

| Enzyme | Day 1 | Day 7 | Day 14 |
| --- | --- | --- | --- |
| No enzyme | 7077 | 5111 | 4175 |
| Seq ID No: 1 | 6990 | 5460 | 4583 |
| F188L, D261G, T288P | 7216 | 5624 | 4656 |
| Y89F, D261G, T288P | 7085 | 6044 | 5151 |
| N86G, Y89M, F188L, D261G, T288P | 7493 | 5349 | 5120 |
| T288P | 7458 | 5785 | 4858 |
| F194S, D261G, T288P | 7746 | 6373 | 5325 |
| D261G, T288P, D372V | 7417 | 5517 | 4525 |
| A192Q, D261G, T288P, S446A | 7357 | 5714 | 5041 |
| A192R, F194L, D261G, T288P, G469R | 7549 | 5536 | no data |
| A192G, D261G, T288P | 7546 | 5815 | no data |
| N86K, F252L, D261G, T288P | 7349 | 5295 | 4775 |
| F194L, D261G, T288P | 7773 | 6803 | 5750 |
| F194S, D261G, T288P, P642Q | 8152 | 5969 | 4971 |
| Y89F, D261G, T288P, I290V, N375S | 7753 | 6175 | 4811 |

The hardness of the cakes increased with storage time. The addition of variants of SEQ ID NO: 1 delayed this increase in hardness as can be seen in Table 3.

TABLE 3

Change in hardness [g] with storage time of cakes with 25 mg protein enzyme per kg flour

| Enzyme | Day 1 | Day 7 | Day 14 |
| --- | --- | --- | --- |
| No enzyme | 647 | 1060 | 1408 |
| Seq ID No: 1 | 677 | 997 | 1171 |
| F188L, D261G, T288P | 683 | 951 | 1167 |
| Y89F, D261G, T288P | 649 | 998 | 1160 |
| N86G, Y89M, F188L, D261G, T288P | 630 | 844 | 1194 |
| T288P | 719 | 1101 | 1098 |
| F194S, D261G, T288P | 672 | 943 | 1061 |
| D261G, T288P, D372V | 593 | 962 | 1344 |
| A192Q, D261G, T288P, S446A | 680 | 931 | 1159 |
| A192R, F194L, D261G, T288P, G469R | 720 | 987 | 1209 |
| A192G, D261G, T288P | 707 | 1024 | 1102 |
| N86K, F252L, D261G, T288P | 678 | 955 | 1248 |
| F194L, D261G, T288P | 648 | 895 | 1050 |
| F194S, D261G, T288P, P642Q | 674 | 1028 | 1316 |
| Y89F, D261G, T288P, I290V, N375S | 602 | 731 | 827 |

The invention claimed is:

1. A method of preparing a high-sucrose dough or a high-sucrose dough-based edible product, comprising adding a polypeptide having maltogenic alpha-amylase activity to the dough, wherein the dough comprises at least 10% sucrose by weight, and the polypeptide:
   a) has an amino acid sequence which is at least 90% identical to SEQ ID NO: 1,
   b) compared to SEQ ID NO: 1 comprises a substitution I15T/S/V/L, R18K, K44R/S/T/Q/N, N86Q/S/T, T87N/Q/S, G88A/S/T, Y89W/F/H, H90W/F/Y/R/K/N/Q/M, W93Y/F/M/E/G/V/T/S, F188H/L/I/T/G/V, D190E/Q/G, A192G/S/T/Q/R, F194S/L/Y, L196F, N371K/R/F/Y/Q or D372E/Q/S/T/A, a deletion of 191 or 192 or an insertion of Ala after 192; and
   c) has more than 20% maltogenic alpha-amylase activity at 10% sucrose by weight compared to its maltogenic alpha-amylase activity in the absence of sucrose.

2. The method of claim 1, wherein the polypeptide is at least 95% identical to SEQ ID NO: 1.

3. The method of claim 1, wherein the polypeptide is at least 97% identical to SEQ ID NO: 1.

4. The method of claim 1, wherein the polypeptide is at least 98% identical to SEQ ID NO: 1.

5. The method of claim 1, wherein the polypeptide is at least 99% identical to SEQ ID NO: 1.

6. The method of claim 1, wherein the polypeptide has the amino acid sequence of SEQ ID NO: 1 with one of the following sets of alterations:

D261G, T288P
F188L, D261G, T288P
T288P
Y89F, D261G, T288P
N86V, F188L, D261G, T288P
Y89F, F188L, D261G, T288P
Y89H, F188L, D261G, T288P
N86T, F188L, D261G, T288P
F194S, D261G, T288P
L196F
D261G, T288P, D372V
Q184H, N187D, F194Y
D190G
N86G, Y89M, F188L, D261G, T288P
F188L, D190G, D261G, T288P
A192Q, D261G, T288P, S446A
F188H
P191*
A192*
A192*, G193*
*192aA
N86K, F252L, D261G, T288P
F194Y, L225S, D261G, T288P
F194L, D261G, T288P
F194S, D261G, T288P, P642Q
D261G, T288P, N375S
F188T
F188G
F188V
A192R, F194L, D261G, T288P, G469R
A192G, D261G, T288P
Y89F, D261G, T288P, I290V, N375S

7. The method of claim 1, wherein the polypeptide is added in an amount corresponding to 1-100 mg enzyme protein per kg of flour.

8. The method of claim 1, wherein the polypeptide is added in an amount corresponding to 5-50 mg per kg of flour.

9. The method of claim 1, wherein the dough comprises above 20% sucrose by weight.

10. The method of claim 1, wherein the dough comprises 30-40% sucrose by weight.

* * * * *

SEQUENCE LISTING

```
<160> NUMBER OF SEQ ID NOS: 1

<210> SEQ ID NO 1
<211> LENGTH: 686
<212> TYPE: PRT
<213> ORGANISM: Bacillus stearothermophilus

<400> SEQUENCE: 1

Ser Ser Ser Ala Ser Val Lys Gly Asp Val Ile Tyr Gln Ile Ile Ile
1               5                   10                  15

Asp Arg Phe Tyr Asp Gly Asp Thr Thr Asn Asn Asn Pro Ala Lys Ser
            20                  25                  30

Tyr Gly Leu Tyr Asp Pro Thr Lys Ser Lys Trp Lys Met Tyr Trp Gly
        35                  40                  45

Gly Asp Leu Glu Gly Val Arg Gln Lys Leu Pro Tyr Leu Lys Gln Leu
    50                  55                  60

Gly Val Thr Thr Ile Trp Leu Ser Pro Val Leu Asp Asn Leu Asp Thr
65                  70                  75                  80
```

```
Leu Ala Gly Thr Asp Asn Thr Gly Tyr His Gly Tyr Trp Thr Arg Asp
                85                  90                  95
Phe Lys Gln Ile Glu Glu His Phe Gly Asn Trp Thr Thr Phe Asp Thr
            100                 105                 110
Leu Val Asn Asp Ala His Gln Asn Gly Ile Lys Val Ile Val Asp Phe
        115                 120                 125
Val Pro Asn His Ser Thr Pro Phe Lys Ala Asn Asp Ser Thr Phe Ala
    130                 135                 140
Glu Gly Gly Ala Leu Tyr Asn Asn Gly Thr Tyr Met Gly Asn Tyr Phe
145                 150                 155                 160
Asp Asp Ala Thr Lys Gly Tyr Phe His His Asn Gly Asp Ile Ser Asn
                165                 170                 175
Trp Asp Asp Arg Tyr Glu Ala Gln Trp Lys Asn Phe Thr Asp Pro Ala
            180                 185                 190
Gly Phe Ser Leu Ala Asp Leu Ser Gln Glu Asn Gly Thr Ile Ala Gln
        195                 200                 205
Tyr Leu Thr Asp Ala Ala Val Gln Leu Val Ala His Gly Ala Asp Gly
    210                 215                 220
Leu Arg Ile Asp Ala Val Lys His Phe Asn Ser Gly Phe Ser Lys Ser
225                 230                 235                 240
Leu Ala Asp Lys Leu Tyr Gln Lys Lys Asp Ile Phe Leu Val Gly Glu
                245                 250                 255
Trp Tyr Gly Asp Asp Pro Gly Thr Ala Asn His Leu Glu Lys Val Arg
            260                 265                 270
Tyr Ala Asn Asn Ser Gly Val Asn Val Leu Asp Phe Asp Leu Asn Thr
        275                 280                 285
Val Ile Arg Asn Val Phe Gly Thr Phe Thr Gln Thr Met Tyr Asp Leu
    290                 295                 300
Asn Asn Met Val Asn Gln Thr Gly Asn Glu Tyr Lys Tyr Lys Glu Asn
305                 310                 315                 320
Leu Ile Thr Phe Ile Asp Asn His Asp Met Ser Arg Phe Leu Ser Val
                325                 330                 335
Asn Ser Asn Lys Ala Asn Leu His Gln Ala Leu Ala Phe Ile Leu Thr
            340                 345                 350
Ser Arg Gly Thr Pro Ser Ile Tyr Tyr Gly Thr Glu Gln Tyr Met Ala
        355                 360                 365
Gly Gly Asn Asp Pro Tyr Asn Arg Gly Met Met Pro Ala Phe Asp Thr
    370                 375                 380
Thr Thr Thr Ala Phe Lys Glu Val Ser Thr Leu Ala Gly Leu Arg Arg
385                 390                 395                 400
Asn Asn Ala Ala Ile Gln Tyr Gly Thr Thr Thr Gln Arg Trp Ile Asn
                405                 410                 415
Asn Asp Val Tyr Ile Tyr Glu Arg Lys Phe Phe Asn Asp Val Val Leu
            420                 425                 430
Val Ala Ile Asn Arg Asn Thr Gln Ser Ser Tyr Ser Ile Ser Gly Leu
        435                 440                 445
Gln Thr Ala Leu Pro Asn Gly Ser Tyr Ala Asp Tyr Leu Ser Gly Leu
    450                 455                 460
Leu Gly Gly Asn Gly Ile Ser Val Ser Asn Gly Ser Val Ala Ser Phe
465                 470                 475                 480
```

```
Thr Leu Ala Pro Gly Ala Val Ser Val Trp Gln Tyr Ser Thr Ser Ala
            485                 490                 495

Ser Ala Pro Gln Ile Gly Ser Val Ala Pro Asn Met Gly Ile Pro Gly
            500                 505                 510

Asn Val Val Thr Ile Asp Gly Lys Gly Phe Gly Thr Thr Gln Gly Thr
        515                 520                 525

Val Thr Phe Gly Gly Val Thr Ala Thr Val Lys Ser Trp Thr Ser Asn
    530                 535                 540

Arg Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
                580                 585                 590

Pro Thr Asn Leu Gly Asp Lys Ile Tyr Leu Thr Gly Asn Ile Pro Glu
            595                 600                 605

Leu Gly Asn Trp Ser Thr Asp Thr Ser Gly Ala Val Asn Asn Ala Gln
        610                 615                 620

Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Phe Ile Lys Arg Ala
                645                 650                 655

Asp Gly Thr Ile Gln Trp Glu Asn Gly Ser Asn His Val Ala Thr Thr
            660                 665                 670

Pro Thr Gly Ala Thr Gly Asn Ile Thr Val Thr Trp Gln Asn
            675                 680                 685
```